United States Patent [19]

Cuppari

[11] Patent Number: 4,909,382

[45] Date of Patent: Mar. 20, 1990

[54] CONTACT LENS CARRYING CASE

[76] Inventor: Pasquale J. Cuppari, 453 High St., Long Branch, N.J. 07740

[21] Appl. No.: 382,423

[22] Filed: Jul. 20, 1989

[51] Int. Cl.$^4$ .............................................. A45C 11/04
[52] U.S. Cl. ..................................... 206/5.1; 206/459; 206/581; 132/294; 132/316; 116/308
[58] Field of Search .................. 206/5.1, 38, 459, 581; 116/280, 307, 308; 132/293, 294, 301, 316

[56] References Cited

U.S. PATENT DOCUMENTS

| | | | |
|---|---|---|---|
| 3,089,500 | 5/1963 | Stalcup | 206/5.1 |
| 3,124,240 | 3/1964 | Croan | 206/5.1 |
| 3,394,717 | 7/1968 | Hollinger | 206/5.1 |
| 4,574,944 | 3/1986 | Gregory | 132/294 |
| 4,823,944 | 4/1989 | Ryder | 206/5.1 |

Primary Examiner—David T. Fidei
Attorney, Agent, or Firm—Richard L. Miller

[57] ABSTRACT

A contact lens carrying case contains two separate sections, each having a pair of lens compartments with screw-on tops, for independently disinfecting and rinsing a pair of contact lenses. The case contains a closable lid with a mirror located therein, and a timer with an alarm for timing the disinfecting and rinsing cycles. Each separate section is removable for cleaning. The case is usable for any contact lens, but is adapted for an AODISC ® catalyst used in SEPTICON ® AND AOSEPT ® systems for soft contact lenses.

4 Claims, 1 Drawing Sheet

CONTACT LENS CARRYING CASE

BACKGROUND OF THE INVENTION

1. Field of the Invention

The instant invention relates generally to apparatus for storing and cleaning contact lenses, and particularly to a carrying case having two distinct and removable compartments, each having a pair of lens containers, for respectively disinfecting and rinsing contact lenses. A timer/alarm device is built into the case, and a mirror is provided.

2. Brief Description of the Prior Art

Contact lenses are now common place, but because of the need for cleanliness and the risk of serious eye disease, the cleaning of the lenses is often a time consuming, delicate, complex and expensive process. It is essential that the lenses be sterile before being placed in the wearer's eye, and the build up of protein and possible contamination from other sources is always of concern to lens wearers. It is important that the cleaning be convenient and thorough, and that a safe place be provided for storage of the lenses. Further, in today's fast paced world, a simple, inexpensive and convenient lens carrier/cleansing case is a practical necessity.

Another problem with contact lenses is that incomplete cleaning or disinfecting of the lenses could cause severe problems to the wearer. Many soft lenses are hydrophilic, and disinfecting the lenses in commonly used hydrogen peroxide solutions for too long or too short a period can cause additional problem. If the time is too short, some of the hydrogen peroxide is retained by the lenses, and could severely damage the eyes. Too long a period softens the lenses and reduces their useful life. A timer and/or alarm device as part of the carrying/disinfecting case is a useful adjunct.

U.S Pat. No. 4,574,944 to Gregory shows a tray device for contact lenses having a working area and a lighted mirror, together with storage for the various liquids, but it does not provide lens carriers or a timer/alarm device. U.S. Pat. No. 4,691,725 to Parisi shows a complex and expensive vibrating tray for cleaning contact lenses. U.S. Pat. No. 4,721,124 relates to a system for storing, cleaning and sterilizing contact lenses using a pump and sprays, the system also being complex and expensive.

SUMMARY OF THE INVENTION

In accordance with the present invention there is provided a contact lens carrying case with two separate sections, each having a pair of closed lens compartments with screw-on tops. One pair of lens compartments is useful for disinfecting the lenses, and the other pair of compartments is useful for rinsing the lenses. The case contains a closable lid with a mirror located therein, and an adjustable timer with an alarm for timing the disinfecting and rinsing cycles. The separate sections are removable for cleaning. The case and compartments are particularly useful for AODISC ® catalysts used in SEPTICON ® and AOSEPT ® systems for soft contact lenses.

It is an object of the present invention to provide a case for carrying and/or cleansing contact lenses which is simple, inexpensive and convenient to carry and to clean.

Another object of the present invention is a contact lens case having a built in timer/alarm for conveniently informing a contact lens user when a disinfecting or other cycle is complete.

A further object of the present invention is a contact lens case which is peculiarly adapted to provide complete cleaning to soft contact lenses and is adapted to use a popular and convenient chemical catalyst system.

These and other objects of the present invention are disclosed hereinafter in conjunction with the accompanying drawings.

BRIEF DESCRIPTION OF THE DRAWING FIGURES

The figures in the drawings are briefly described as follows.

DESCRIPTION OF THE PREFERRED EMBODIMENT

Figure 1:
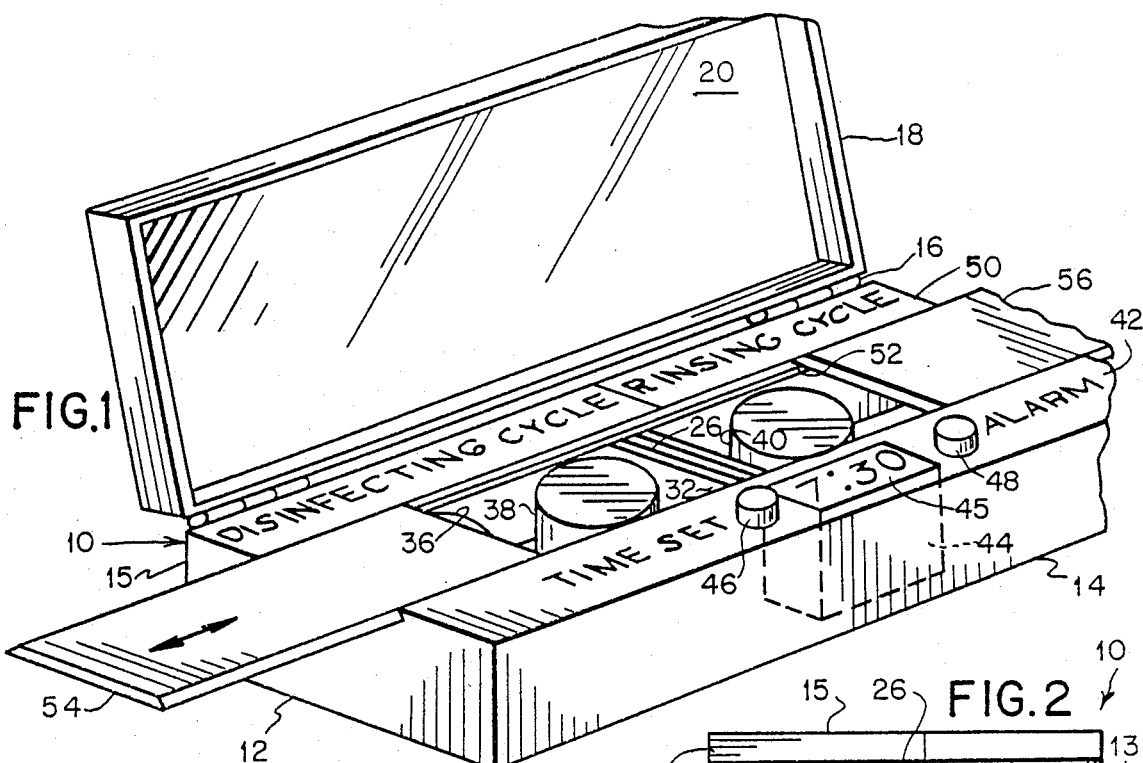
FIG. 1 is a diagrammatic perspective view of the present invention.
Figure 2:
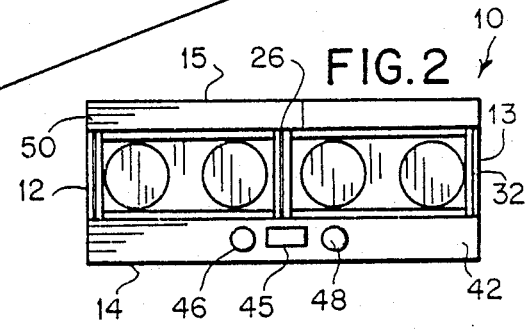
FIG. 2 is a diagrammatic top plan view of the base of the contact lens carrying case with the lid and slide covers removed therefrom.

The contact lens carrying case comprises a rectangular, walled container 10 having a pair of side walls, 12, 13 and a pair of front and back walls 14, 15. Connected to the back wall 15 via conventional hinges 16 is a lid 18 into which is secured a mirror 20. The case and lid are preferably constructed from a suitable strong and easily cleanable plastic such as polyethylene, but other plastics or materials may be used. Light weight, low cost and ease of fabrication are other considerations.

Figure 5:
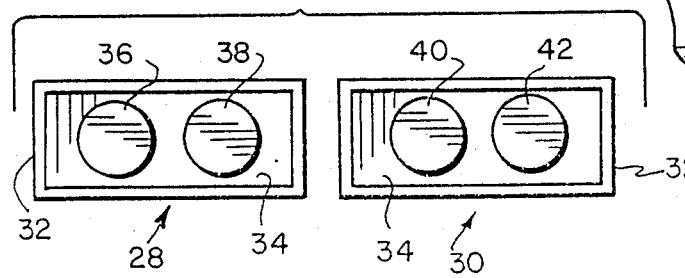
FIG. 5 is a plan view of the lens containers.
Figure 6:
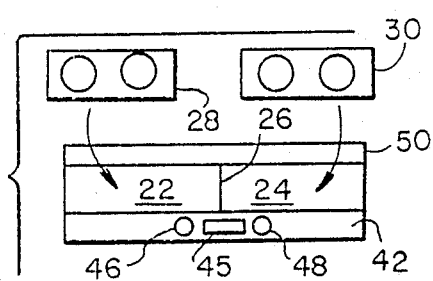
FIG. 6 is a diagrammatic view of the case with the lens compartments removed therefrom.

The container 10 has a pair of internal cavities 22 and 24 as best shown in FIG. 6, with a wall 26 situated therebetween, the cavities being constructed to admit and firmly support a pair of liner sections constructed to admit and firmly support a pair of liner sections 28 and 30 as best illustrated in FIG. 5, having rectangular side walls 32 and a floor 34. In each of the liner sections 28 and 30 are a pair of cylindrical lens carriers 36, 38, 40 and 42 to be described in detail subsequently.

Mounted along the top of case 10 between side walls 12 and 13 and along front wall 14 is a plastic or metal strip 42 into which is secured a timer device 44 including a display 45, a button 46 to set the time, and a button 48 to actuate an alarm such as a buzzer at the expiration of the time set into timer 44. Also mounted along back wall 14, is a strip of material 50 which may, if desired, be hinged to define a storage compartment thereunder. The inside edges of the strips 42 and 50 may be formed to have indentations 52 therein to receive slidable covers 54 and 6 which serve to cover the cavities 22 and 24. Batteries for timer 44 may be secured in known fashion beneath strip 42 or along wall 14.

Figure 3:
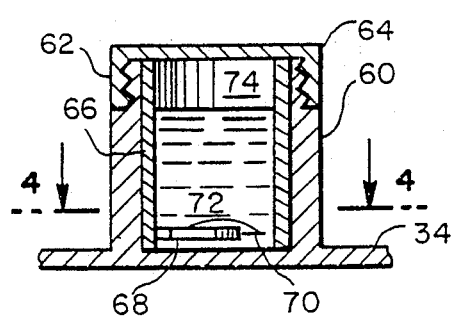
FIG. 3 is a vertical cross-sectional elevational view of one of the containers shown broken away from the case.
Figure 4:
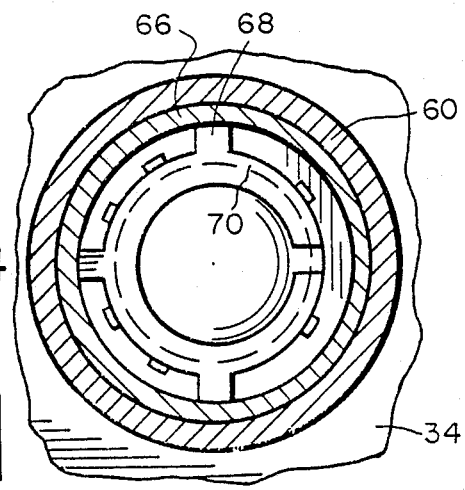
FIG. 4 is an enlarged cross-sectional elevational view taken along line 4—4 of FIG. 3 with a contact lens illustrated therein in phantom.

FIGS. 3 and 4 show he construction of the lens carriers 36, 38, 40 and 42. Carriers 36 and 38 are preferably used for disinfecting the contact lenses, while carriers 40 and 42 are preferably for rinsing the contact lenses. A cylindrical sidewall 60 extends upward from the floor 34 and has a threaded portion 62 on the outside thereof adapted to mate with the threaded inside of cap or cover 64 which is removably secured to sidewall 60. A removable sleeve 66 may be inserted within the carrier adjacent the wall 60 thereof. For soft contact lenses and AODISC® 68 is placed within the carrier, and the contact lens 70, shown in phantom in FIG. 4, is placed within the carrier. The carrier is then filled with the desired fluid 72 with a space 74 of about ¾" left between the fluid 72 and the cover 64, and cover 64 is secured on top of the carrier as shown in FIG. 3.

In use, the contact lenses to be cleaned are first placed carefully in disinfecting carriers 36 and 38, and a 0.9% saline solution containing 3% hydrogen peroxide ($H_2O_2$) is added. The platinum catalyst such as AODISC® 68 will disinfect the lenses in six hours. The timer 44 is set for at least six hours by adjusting button 46, and the alarm may be set by adjusting button 48. Disinfecting is complete when the alarm sounds. Since the $H_2O_2$ takes at least six hours to convert to $H_2O$ and $H_2$, removing the lenses prior to the six hour period would mean than some $H_2O_2$ could remain on the lenses, and could burn the eyes if the lenses are inserted into the eyes without proper rinsing.

After disinfecting the lenses, the lenses are carefully removed from carriers 36 and 38 and placed in carriers 40 and 42 together with a 0.9% saline solution or other appropriate rinsing agent. The timer 44 and alarm 48 may be set as previously. The carriers 40 and 42 may, with the appropriate solution added therein, be used to store the lenses until they are needed again. Obviously an AODISC® may be used in carriers 40 and 42 if desired.

The contact lens carrying case and cleaning apparatus disclosed herein may be used with any type of cleaning or disinfecting solution, and is not limited to the AODISC® system. Information as the AODISC® system may be found in U.S. Pat. No. 3,912,451.

While the invention has been described in conjunction with a preferred embodiment thereof, it is apparent that changes may be made to the construction and operation thereof without departing from the scope of the invention as hereinafter claimed.

What is claimed is:

1. A container and carrying case for contact lenses comprising
   (a) a walled container having an open top and first and second internal cavities and at least one compartment;
   (b) a removable cover for each of said cavities;
   (c) a lid hinged to a wall of said container and adapted to close over the top of said container;
   (d) a mirror secured to the inside of said lid;
   (e) first and second walled open topped liner sections adapted to fit securely within said first and second internal cavities;
   (f) first and second open topped cylindrical lens carriers mounted on each of said liner sections, each of said lens carriers having a cylindrical wall with a threaded top portion and a threaded cap adapted to be secured by screwing onto the top of said cylindrical wall to provide a closed cavity within each said lens carrier; and,
   (g) timer means including a time display, a time set mechanism and an alarm set mechanism located within a compartment in said container and accessible to a user thereof.

2. A contact lens container as in claim 1 in which each said liner section has a floor portion, and in which each said lens carrier extends from said floor portion such that the floor portion forms the bottom of each said lens carrier.

3. A contact lens container as in claim 2 and including a removable sleeve-shaped liner adapted to fit within each said lens carriers along the inside of said cylindrical wall.

4. A contact lens holder as in claim 1 in which at least each of the said first and second lens carriers mounted on one of the said liners is adapted to contain a coated catalytic disc therein.

* * * * *